United States Patent [19]

Farber

[11] Patent Number: 5,659,126
[45] Date of Patent: Aug. 19, 1997

[54] GAS CHROMATOGRAPH TECHNIQUES FOR ON-LINE TESTING OF TRANSFORMER FAULTS

[76] Inventor: Milton Farber, 1335 Old Mill Rd., San Marino, Calif. 91108

[21] Appl. No.: 635,367

[22] Filed: Apr. 19, 1996

[51] Int. Cl.⁶ .......................... G01N 7/00; G01N 31/06; B01D 57/00
[52] U.S. Cl. .......................... 73/19.02; 422/80; 422/89; 73/19.05; 73/23.38; 73/23.35
[58] Field of Search .................... 73/19.02, 19.01, 73/19.05, 19.11, 19.1, 23.38, 23.35; 422/80, 82.04, 89

[56] References Cited

U.S. PATENT DOCUMENTS

| | | | |
|---|---|---|---|
| Re. 31,246 | 5/1983 | Adrian et al. | 250/343 |
| 2,333,934 | 11/1943 | Jacobson | 23/232 |
| 2,962,894 | 12/1960 | Banks et al. | 73/155 |
| 3,068,686 | 12/1962 | Harmon | 73/23 |
| 3,150,516 | 9/1964 | Linnenbom et al. | 73/19 |
| 3,171,273 | 3/1965 | Dijkema | 73/19 |
| 3,339,346 | 9/1967 | Buchanan | 55/195 |
| 3,357,257 | 12/1967 | Herndon et al. | 73/421.5 |
| 3,524,351 | 8/1970 | Bayly et al. | 73/421 |
| 3,624,710 | 11/1971 | Carter | 73/61.1 R |
| 3,680,359 | 8/1972 | Lynch | 73/27 R |
| 3,715,910 | 2/1973 | Fore et al. | 73/23.1 |
| 3,759,086 | 9/1973 | McAuliffe | 73/19 |
| 3,792,272 | 2/1974 | Harte et al. | 250/343 |
| 3,844,160 | 10/1974 | Yamaoka | 73/19 |
| 3,921,457 | 11/1975 | Barnes, Jr. et al. | 73/421.5 R |
| 3,927,978 | 12/1975 | Wasik | 23/230 R |
| 3,992,155 | 11/1976 | Nilsson | 23/254 E |
| 4,003,257 | 1/1977 | Fletcher et al. | 73/23.1 |
| 4,058,373 | 11/1977 | Kurz et al. | 55/16 |
| 4,090,392 | 5/1978 | Smith et al. | 73/421.5 R |
| 4,112,737 | 9/1978 | Morgan | 73/23 |
| 4,154,086 | 5/1979 | Button et al. | 73/19 |
| 4,236,404 | 12/1980 | Ketchum et al. | 73/19 |
| 4,257,257 | 3/1981 | Dairaku et al. | 73/19 |
| 4,319,479 | 3/1982 | Iwamura et al. | 73/19 |
| 4,437,082 | 3/1984 | Walsh et al. | 336/58 |
| 4,444,040 | 4/1984 | Sakai et al. | 73/19 |
| 4,461,165 | 7/1984 | Kesson | 73/19 |
| 4,484,483 | 11/1984 | Riegger et al. | 73/864.23 |
| 4,578,244 | 3/1986 | Cosgrove, Jr. et al. | 422/65 |

(List continued on next page.)

FOREIGN PATENT DOCUMENTS

0565248A2  10/1993  European Pat. Off. .

OTHER PUBLICATIONS

P. J. Griffin, "Criteria for the Interpretation of Data for Dissolved Gases in Oil from Transformers (A Review)," 1988, pp. 89–106.

Primary Examiner—Hezron E. Williams
Assistant Examiner—J. David Wiggins
Attorney, Agent, or Firm—Christie, Parker & Hale, LLP

[57] ABSTRACT

A gas chromatograph measures the gas concentration levels of fault gases contained in the gas within a headspace above the electrical insulating oil supply contained in a power transformer. An on-line fault detection system involves gas samples taken from transformers at a utility site in sequence with automatically controlled timer valves which open to draw a gas sample from each transformer headspace and then transfer the gas directly to a single gas chromatograph. The gas chromatograph includes an integrator which calculates the concentration level of each fault gas in the gas sample. The resulting fault gas data are fed to a computer programmed with a partition function based on Henry's Law to convert the headspace fault gas data to fault gas concentration levels within the transformer oil. This produces gas fault analysis data which are used to provide an early warning of specific transformer problems correlated to, indicative of and detected by excessive dissolved fault gas concentration levels in the oil identified with particular transformer faults. The invention avoids costly and time consuming prior art analysis techniques of extracting fault gases from the oil sample in an independent operation before the concentration levels can be measured.

27 Claims, 6 Drawing Sheets

U.S. PATENT DOCUMENTS

| | | | |
|---|---|---|---|
| 4,587,834 | 5/1986 | Fisher | 73/23.1 |
| 4,731,732 | 3/1988 | Warchol et al. | 364/510 |
| 4,763,514 | 8/1988 | Naito et al. | 73/19 |
| 4,764,344 | 8/1988 | Knab | 422/89 |
| 4,890,478 | 1/1990 | Claiborne et al. | 73/19 |
| 4,922,747 | 5/1990 | Wall | 73/61.1 R |
| 4,944,178 | 7/1990 | Inoue et al. | 73/19.1 |
| 4,993,271 | 2/1991 | Vargason | 73/863.33 |
| 4,997,770 | 3/1991 | Giles et al. | 436/132 |
| 5,115,666 | 5/1992 | Williams | 73/19.1 |
| 5,127,259 | 7/1992 | Kahl et al. | 73/19.1 |
| 5,144,831 | 9/1992 | Hale et al. | 73/19.05 |
| 5,233,876 | 8/1993 | LaPack et al. | 73/863.23 |
| 5,243,848 | 9/1993 | Cox et al. | 73/19.05 |
| 5,400,641 | 3/1995 | Selmon et al. | 73/19.01 |
| 5,442,948 | 8/1995 | Cowing | 73/19.05 |
| 5,528,923 | 6/1996 | Ledez et al. | 73/19.12 |

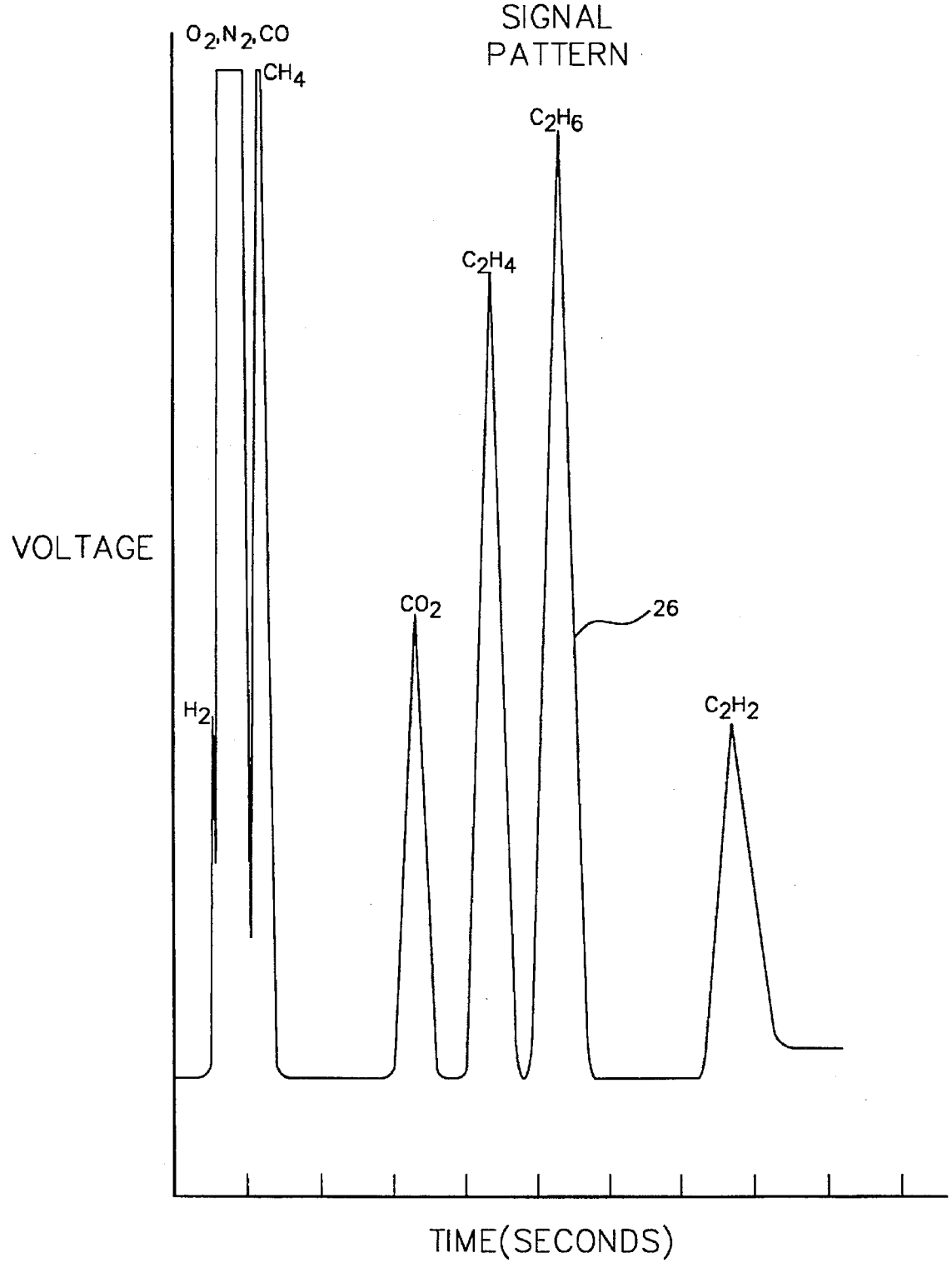

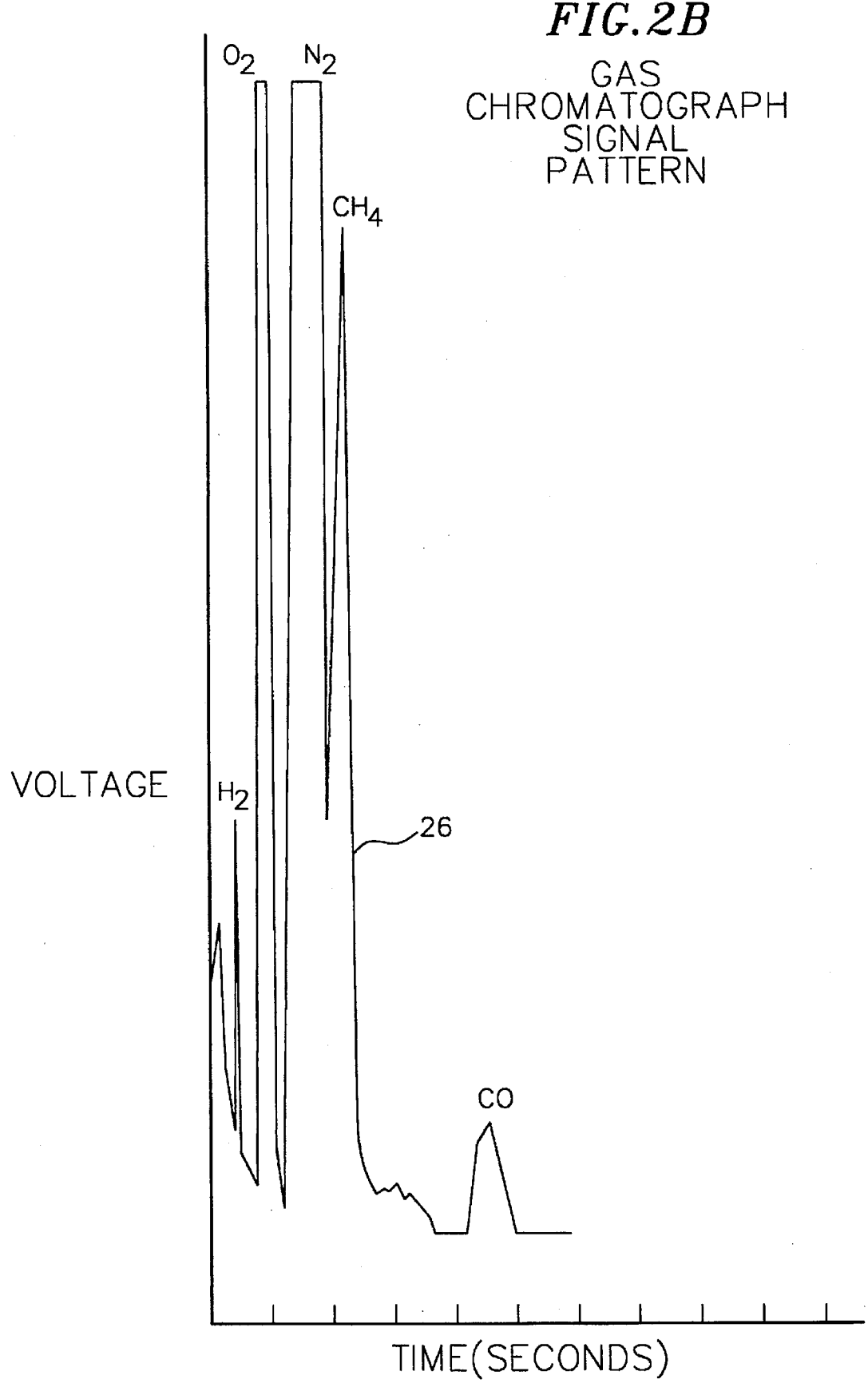

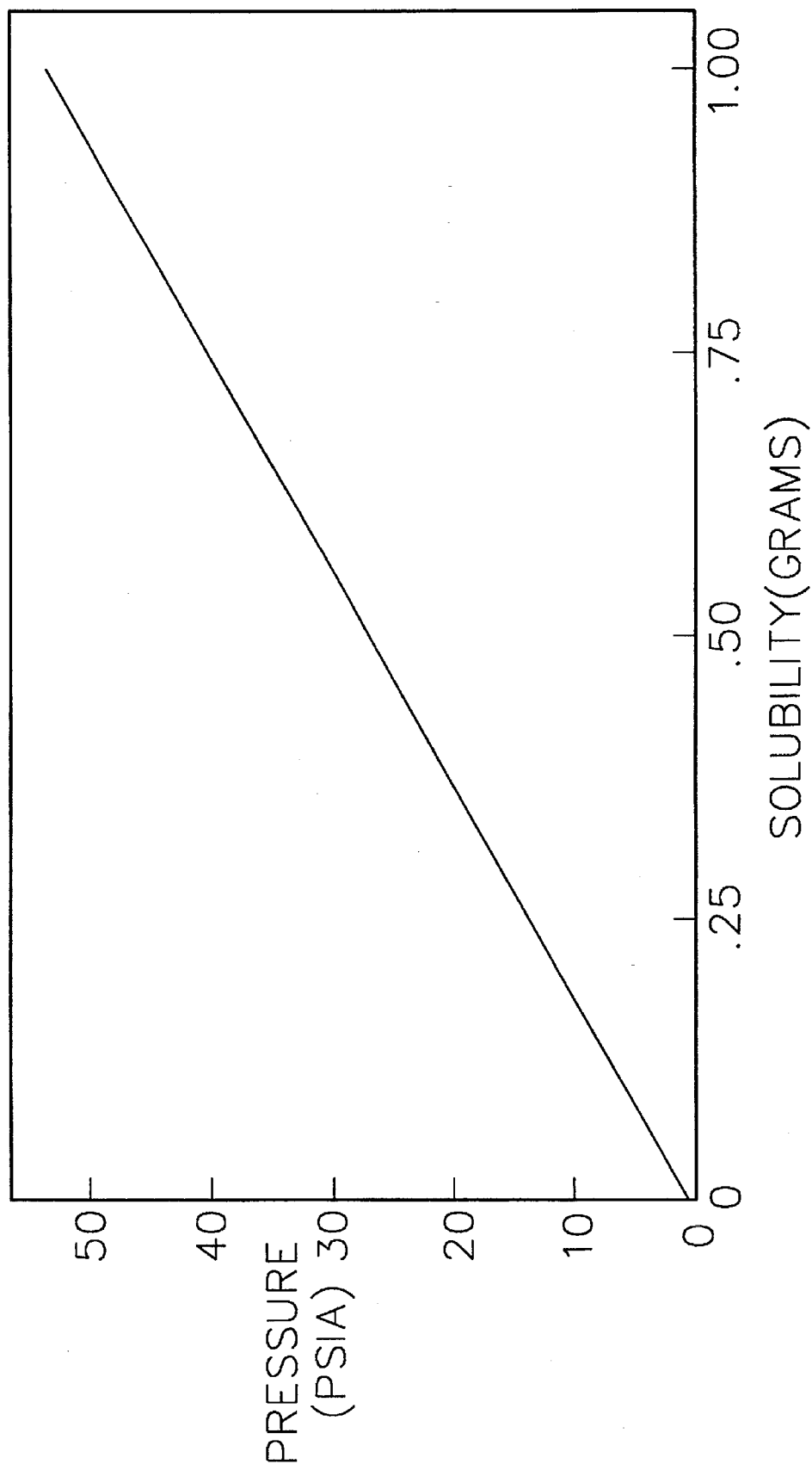

GAS CHROMATOGRAPH TECHNIQUES FOR ON-LINE TESTING OF TRANSFORMER FAULTS

FIELD OF THE INVENTION

This invention relates to fault detection in electrical transformers, and more particularly to an on-line system for early detection of faults in large power transformers of the type containing electrical insulation oil for the transformer coils.

BACKGROUND OF THE INVENTION

It has been a common problem in the electrical utility industry to analyze dissolved gas concentrations in the electrical insulating oil of the so-called oil-immersed transformers. If faults occur within the transformer, such as from arcing, pyrolysis (overheating), corona discharge, and the like, certain gases are evolved into the oil supply. Fault gases that have been recognized in the past as identifying specific transformer faults have included ethane, ethylene, acetylene, methane, carbon dioxide, carbon monoxide, hydrogen and oxygen. Increases in fault gas concentration levels in the transformer oil can be measured to identify specific types of malfunctions as well as their severity. If a transformer problem is allowed to go undetected, the electrical utility can suffer extremely high replacement costs. Worker safety also is a major concern because of the explosive nature of certain fault gases, such as acetylene, hydrogen and carbon monoxide any of which may react with oxygen. Reliable detection of such fault gases before the concentration levels become dangerously high is an objective of the present invention.

Electrical utilities normally send a person to the transformer site to regularly collect oil samples and return them to a laboratory for testing the fault gas concentration levels. If a particular fault gas exceeds a certain level, it will be a warning of a particular fault which can then be corrected.

The present invention is based on a recognition that periodic checking of oil samples from large power transformers may not occur often enough to detect a problem until it is too late for reasonable corrective action. The present invention solves the problem by providing continuous on-line fault gas concentration data from the transformer site that can be constantly monitored to detect a problem the moment it arises.

In the past, gas chromatograph techniques have been used to measure fault gases extracted from oil samples. One standard technique for detecting fault gases in transformers has involved use of a mercury Toepler pump method of gas extraction. Such analytical techniques require expensive laboratory equipment, and the complete analysis is time consuming. There is also a danger in working with large amounts of mercury in glassware that is under high vacuum in order to extract the gases from the oil sample. In addition, oil samples containing very low levels of certain gases cannot provide enough gas to perform accurate chromatographic analyses. Handling of oil samples also can result in the loss of certain volatile gases such as hydrogen.

In another prior method of measuring fault gases, an oil stripper column is inserted in the oven chamber of a gas chromatograph. An argon carrier gas is used for the stripping process. The laboratory equipment is expensive, and the process to analyze gas samples is slow. Since gas solubilities vary with temperature, the extraction efficiencies, which are different at the test temperature compared to room temperature, contribute to inaccuracies in measurements for certain gases. Discrepancies for certain gas measurements have been found when test results from this method are compared with the mercury Toepler pump extraction method.

Thus, there is a need for a transformer fault gas detection system which can analyze fault gases with extreme accuracy, and in which such analysis is accomplished at a reasonably low cost and without the delay times caused by oil sample extraction and analysis and the complex equipment associated with commonly used fault gas analytical techniques.

SUMMARY OF THE INVENTION

Briefly, one embodiment of the invention comprises a method for monitoring dissolved gases in the electrical insulating oil supply of an electrical transformer in which a blanket of gas containing a fault gas is present in the headspace above the insulating oil supply contained in the transformer. The method includes transferring a sample of the gas from the headspace to a gas chromatograph instrument, and measuring by gas chromatograph techniques the gas concentration level of the fault gas contained in the gas sample taken from the transformer headspace. The output from the gas chromatograph is processed by a computing device for calculating the related gas concentration level of the fault gas which is present in the oil supply. The computing device is informed of a partition function based on Henry's Law and converts the measured fault gas concentration level in the headspace to a measurement of the corresponding concentration level of the same fault gas in the oil supply. The resulting data are used for producing a reading of the fault gas concentration in the transformer oil supply to provide an indication of a specific transformer fault.

The present invention provides a simpler and faster method for measuring fault gas concentration levels because it avoids the time-consuming and complex task of extracting fault gases from an oil sample. Instead, the headspace gas sample is used directly in the gas chromatograph to measure the fault gas concentration level, and the output data are simply converted mathematically to a corresponding fault gas concentration value known to be present in the oil supply, given the relationship based on Henry's Law. The method also is safer than the mercury Toepler pump method because there is no danger in working with large amounts of mercury. The analytical results also are considered more accurate, especially for fault gases that normally occur in minute concentration levels in the oil.

These and other aspects of the invention will be more fully understood by referring to the following detailed description and the accompanying drawings.

BRIEF DESCRIPTION OF THE DRAWINGS

FIGS. 2A and 2B are graphs showing signal pattern outputs from a gas chromatograph.

FIG. 3 is a graph showing a linear relationship between solubility of ethane in transformer oil as a function of absolute pressure.

DETAILED DESCRIPTION

Figure 1:
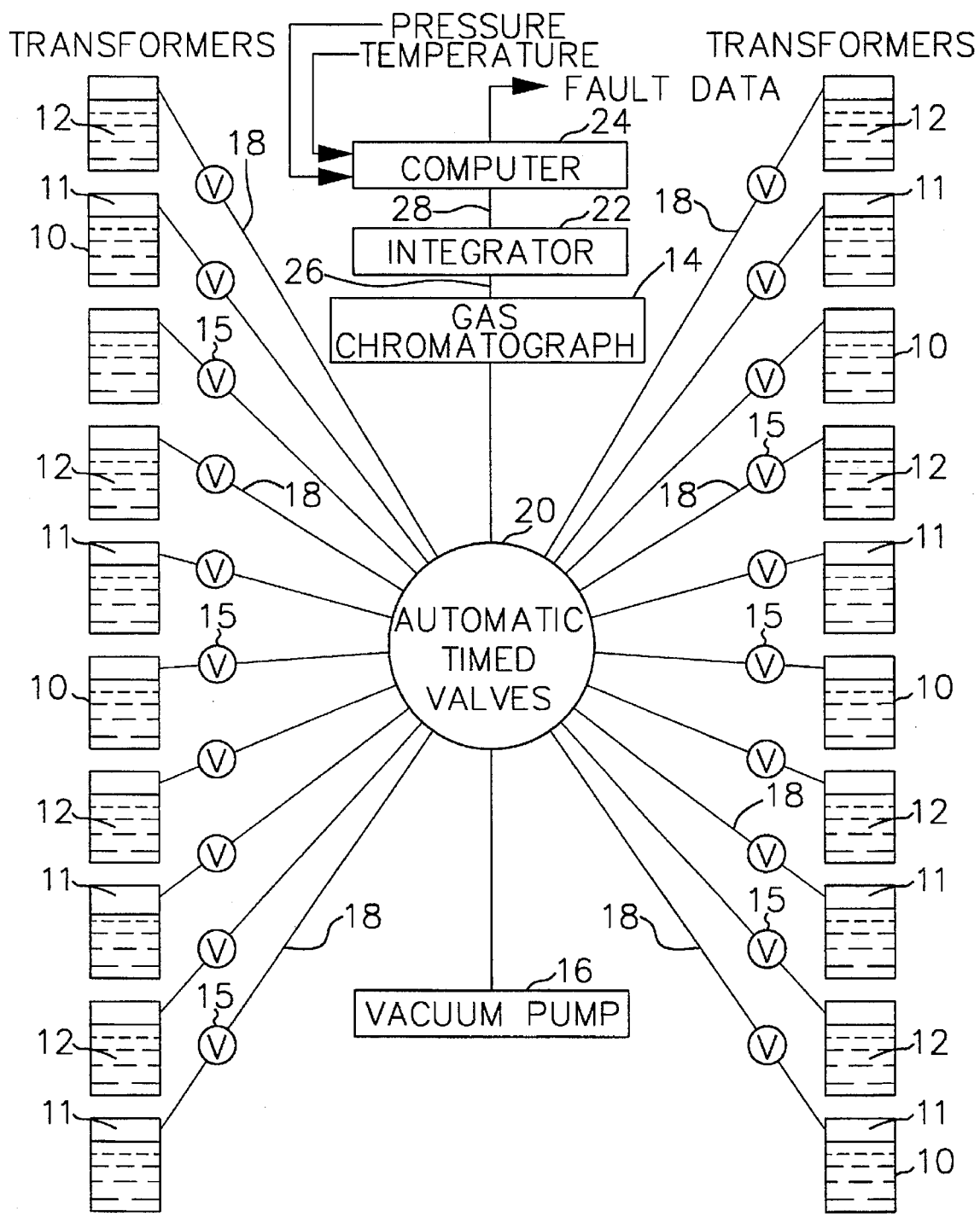
FIG. 1 is a schematic diagram illustrating an on-line transformer fault gas detection system according to principles of this invention.

FIG. 1 schematically illustrates a large electrical utility distribution system having, by way of example, a group of twenty large power transformers 10. The invention has to do with measuring fault gas concentrations present in the headspace 11 within the transformer above the transformer oil supply 12. The invention applies the principle of Henry's Law which states that gas concentrations in the oil and in the headspace above it will equalize to a known concentration ratio which is unique to each particular fault gas. In the present invention, gas concentrations of fault gases in the headspace are measured to identify certain faults within the transformer in the same way that gas concentration levels in the fault gases contained in the transformer oil sample can be measured to detect the same faults.

The present system includes the use of a single gas chromatograph 14 to measure the concentrations of fault gases present in the gas sample taken from the headspace 11 above the oil supply 12 in each transformer. Fault gases commonly present in the gas sample include ethane ($C_2H_6$), ethylene ($C_2H_4$), acetylene ($C_2H_4$), methane ($CH_4$), carbon dioxide ($CO_2$), carbon monoxide (CO), oxygen and hydrogen. Dry nitrogen is separately added to the headspace.

The gas samples are taken one transformer at a time with automatic control valves 15 opening in sequence to access each headspace. A vacuum pump 16 initially evacuates a line 18 to each transformer being accessed, followed by operation of a central timer valve 20 which automatically opens the valve 15 to draw a gas sample from the transformer headspace into the gas chromatograph 14. The gas chromatograph includes an integrator 22 which processes the data output signal pattern from the gas chromatograph and calculates the concentration of each fault gas contained in the gas sample. The resulting fault gas data from the integrator are fed into a computer 24 for converting the measured fault gas levels present in the gas sample to related fault gas levels in the oil supply. A continuous data output showing the fault gas concentration levels in the oil can be used to determine if a fault condition exists. The computer also can be programmed to provide a warning if any particular fault gas concentration exceeds a safe level.

The fault gas-containing gas sample transmitted from the headspace of the transformer to the input of the gas chromatograph analysis device is processed by the control logic of the gas chromatograph which operates in a familiar manner well known to those skilled in the art. The gas chromatograph of this invention is preferably a device which uses nitrogen as the carrier gas and includes a discharge ionization detector which produces output signal patterns 26 similar to those shown in FIGS. 2A and 2B. These output signal data can be obtained using a Poropak column for the hydrocarbon gases as shown in FIG. 2A. Hydrogen, oxygen, carbon monoxide and nitrogen data can be obtained with a Molsieve column as shown in FIG. 2B. Gas chromatographs used in transformer oil analysis usually use two columns in series, usually a Poropak and Molsieve column. The gas chromatograph can be used with argon or helium as carrier gases, as well as nitrogen. Gas chromatographs using flame ionization detectors are not suitable for utilities because of the need to avoid hydrogen gas in the vicinity. The output signal pattern from the gas chromatograph is a voltage measurement for each detected fault gas having a magnitude and time related value that can be processed to determine the gas concentration level for each fault gas within the gas sample. The output signal from the gas chromatograph is integrated by the integrator 22 to produce an output signal 28 representing the amount or volume of each fault gas contained in the gas sample. The output from the integrator is preferably measured in parts per million (ppm) of the fault gas per volume of gas in the gas sample.

The measured concentration levels of the fault gases contained in the headspace gas sample are then transmitted as inputs to the computer device 24 which converts the fault gas data inputs to corresponding gas concentration levels in the transformer oil supply. This is accomplished by calculating a "partition function" for each fault gas based on Henry's Law. The partition function is used to convert the measured gas concentration level of each fault gas in the headspace to a corresponding measurement of the concentration level of the same fault gas in the, transformer oil supply. The calculated fault gas concentration levels present in the oil supply are then used to determine whether specific transformer fault conditions exist. These measurements can be carried out rapidly and continuously so as to provide continuing fault gas level measurements in each of the transformers in sequence repeated continuously over time. The computer also can be programmed with incipient fault gas data representing ppm values for each fault gas that indicate a specific fault condition level. The incipient fault gas data are preferably determined as a function of a specific temperature and pressure to be compared with the calculated fault gas data in the oil sample. A display can indicate all comparative data in real time and an alarm can be activated if any detected fault gas measurement exceeds a preset incipient fault gas level. Further analysis of fault gas data as they relate to transformer problems are discussed in Griffin, *Electrical Insulating Oils*, ASTM, 1988, pp 89–106, incorporated herein by reference.

The partition function is a mathematical ratio of ppm of gas in the gas space divided by ppm of gas in the oil. The ratio is determined from known gas solubility information (the solubility of each fault gas in transformer oil at a known oil temperature and gas pressure). Gas solubility in oil varies as a function of temperature of the oil supply and as a function of the gas pressure. The temperature and pressure measurements for each transformer under test are inputs to the computer which is programmed to process these inputs to calculate the related partition function for the given temperature and pressure. Oil density and coefficients of expansion (which vary depending on temperature and pressure) also can be inputs to the computer program. The calculated partition function is then used to determine the fault gas concentration in the oil supply.

EXAMPLE 1

Preliminary experiments for developing this present method for measuring fault gases from transformer oil were necessary to establish the validity of the method and its reliability compared to the current methods of transformer oil fault gas analysis. The solubility of nine gases ($C_2H_6$, $C_2H_4$, $C_2H_2$, $CO_2$, $CH_4$, $CO$, $N_2$, $O_2$ and $H_2$) in the transformer oil was measured as a function of temperature from 0° C. to 200° C. To do this experimentally a 150 milliliter stainless steel bulb was partially filled with a new transformer oil. The actual weight of oil used for each gas depended on the solubility of that gas, being greater for less soluble gases. The stainless steel bulb with the necessary amount of oil in it was pumped down with a vacuum pump and then the sample of the pure gas whose solubility is to be determined was introduced at a known pressure on the attached gauge (usually 30 to 60 psig) and temperature. Thus, the absolute quantity of both gas and oil was known. Using an oven, the 150 ml bulb was heated, and the pressure read on the gauge after shaking, at 25° C. steps. From the pressure readings and the known weight of oil, the gas solubility was calculated at about eight different temperatures. An ice and water mixture was used to cool the system for the 0° C. readings. A thermocouple was used to measure the bulb temperature.

Initially, the ideal gas law validity was confirmed for the linearity of solubility as a function of the absolute pressure.

A pressure-solubility study of ethane in transformer oil was made from 1 atm to 4 atm at 27° C. Linearity was observed, as shown in FIG. 3.

Following this investigation, absolute solubility studies of the transformer oil gases were conducted as a function of temperature from 0° C. to 200° C. A 100 gram oil sample was placed in a 150 cc stainless steel bulb. After evacuation approximately 3 to 4 atm of gas was introduced into the system and the solubility determined by pressure measurements. The 0° C. measurement was made in an ice bath, while the higher temperature measurements were made by inserting the bulb into an oven. Continuous shaking of the bulb for 5 to 10 minutes produced constant readings on the pressure gauges, indicating solubility equilibrium had been reached. It was necessary to make corrections for the various expansions. Corrections for the oil expansion were based on a coefficient of volume expansion, $\alpha$, of $8 \times 10^{-4}$ cc/°C. The volume expansion of the stainless steel bulb was less than 10% of the oil expansion. Since oil expansion correction was on the order of 10% or less the stainless steel correction was neglected. The ideal gas law correction $$\left( p = \frac{RT}{V}, R = 0.0821 \text{ liter } atm/°K. \right)$$

was made for the gas above the oil.

The quantity of gas dissolved in the oil is the difference between the quantity introduced and the quantity remaining as gas at equilibrium (after shaking). Calculation of solubility points for other gases is done in a similar way.

The solubility was corrected at each temperature to a pressure of 1 atm (14.7 psia). An oil specific gravity of 0.87 was used for the volume-mass conversion of the oil.

Figure 4:
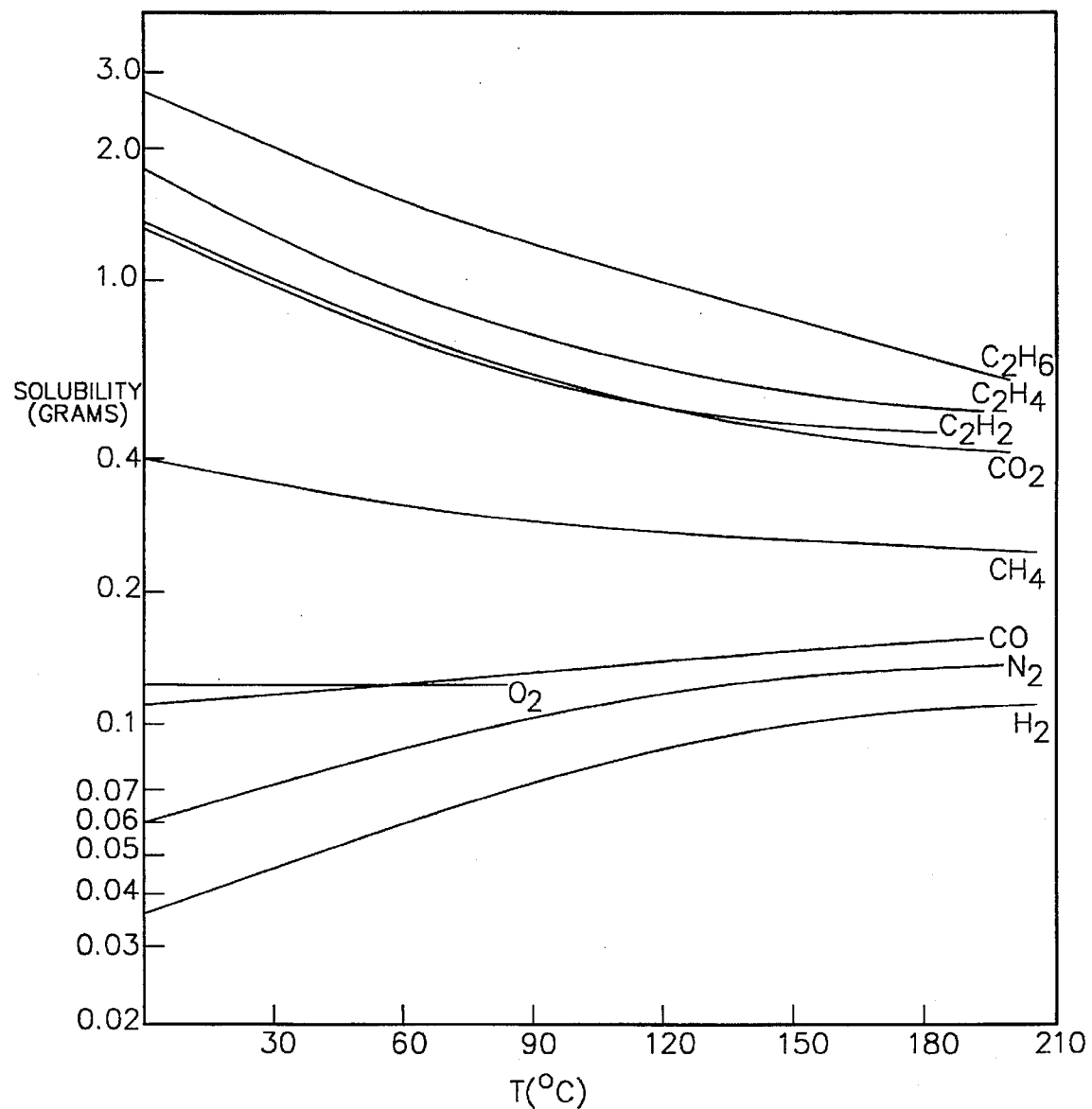
FIG. 4 is a graph showing solubility versus temperature relationships for nine separate fault gases.

The complete solubility data obtained consisted of nine solubility curves for individual fault gases represented on a composite semilogarithmic graph shown in FIG. 4. Of these gases it can be seen that $C_2H_6$ was the most soluble and $H_2$ was the least soluble, for example.

In addition to the graphs shown in FIG. 4, the solubilities were reduced to mathematical form, i.e., equations of the type $$Solubility = p(Ae^{-kT} + BT + CT^2) \text{ cc of gas/cc of oil}$$

where T is the Celsius temperature, p=pressure in atm, and k, A, B and C are constants for each gas. These equations can be programmed into the computer for determination of the quantities of the nine gases dissolved in transformer oil at a given temperature and pressure. Eight of the equations are presented in Table 1.

TABLE 1

| Mathematical Equations for Solubility of Gas in Oil (cc gas/cc oil) | |
|---|---|
| $C_2H_6$ | $S = 3.2e^{-0.0116T} + 0.001 \, T^2 \times 10^{-2}$ |
| $C_2H_4$ | $S = 1.79e^{-.010T} + .0007 \, T^2 \times 10^{-2}$ |
| $CO_2$ | $S = 1.38e^{-.010T} + .0013 \, T$ |
| $C_2H_2$ | $S = 1.29e^{-.010T} + .0013 \, T$ |
| $CH_4$ | $S = 0.39e^{-.004T} + .0003 \, T$ |
| $CO$ | $S = 0.111e^{+0.002T}$ |
| $N_2$ | $S = 0.060e^{-0.0065T} - T^3 \times 10^{-8}$ |
| $H_2$ | $S = 0.037e^{-0.0078T} - 0.05 \, T^3 \times 10^{-8}$ |

For oxygen S is a constant up to 80° C. A chemical reaction occurs above 80° C. For oxygen S=0.125 cc gas/cc oil.

As examples of the accuracy of the fit of the equations to the curves, the following Tables 2 and 3 provide a comparison of the solubility values at 90° C. and 180° C. from the equations and from the graphs for eight gases.

TABLE 2

| (Solubility at 90° C. in cc gas/cc oil) | | | |
|---|---|---|---|
| Gas | Equation | Graph | Difference |
| $C_2H_6$ | 1.207 | 1.22 | -1.07% |
| $C_2H_4$ | 0.784 | 0.77 | +1.80 |
| $CO_2$ | 0.678 | 0.65 | +4.30 |
| $C_2H_2$ | 0.642 | 0.635 | +1.10 |
| $CH_4$ | 0.299 | 0.300 | -0.33 |
| $CO$ | 0.133 | 0.134 | -0.75 |
| $N_2$ | 0.1004 | 0.0995 | +0.90 |
| $H_2$ | 0.0711 | 0.071 | +0.14 |

TABLE 3

| (Solubility at 180° C. in cc gas/cc oil) | | | |
|---|---|---|---|
| Gas | Equation | Graph | Difference |
| $C_2H_6$ | 0.7205 | 0.67 | +7.5% |
| $C_2H_4$ | 0.523 | 0.525 | +0.38 |
| $CO_2$ | 0.462 | 0.445 | +3.8 |
| $C_2H_2$ | 0.447 | 0.469 | -4.7 |
| $CH_4$ | 0.244 | 0.258 | -5.4 |
| $CO$ | 0.159 | 0.156 | +1.9 |
| $N_2$ | 0.135 | 0.137 | -1.5 |
| $H_2$ | 0.121 | 0.109 | +11.0 |

Partition ratios (ppm of gas in gas space divided by ppm of gas in oil) were calculated from the measurements taken to determine solubilities and are presented in Table 4 for an oil temperature of 25° C.

TABLE 4

| Solubility Partition Comparison | |
|---|---|
| Gas | Partition Ratio (ppm of gas in gas space/ppm of gas in oil) |
| $O_2$ | 7.9 |
| $N_2$ | 13.6 |
| $CO_2$ | 0.97 |
| $CO$ | 9.6 |
| $H_2$ | 22.2 |
| $CH_4$ | 2.78 |
| $C_2H_6$ | 0.442 |
| $C_2H_4$ | 0.73 |
| $C_2H_2$ | 0.97 |

Thus, the partition function used in the computer for calculating fault gas concentration levels in the oil can be generated from equations similar to those shown in Table 1; or the partition function can be generated using the solubility curve data. In either instance, temperature and pressure data are obtained from the transformer under analysis and used as inputs to calculate the partition function for each fault gas since the partition ratios are temperature and pressure dependent.

EXAMPLE 2

The following is a laboratory test used to confirm the accuracy of this invention in measuring fault gas levels in transformer oil, using as a sample the gas in a gas space above the oil.

Availability of measurements of the solubilities of the nine gases, presented above, made possible a simpler method of measuring the quantities of these gases in the oil from actual transformers. In practice the oil sample from the transformer is received in a 150 cc stainless steel bulb. The basic idea of this method is to shake about 75 cc of the oil sample in the SS bulb for a few minutes to allow the gases to reach an equilibrium between the dissolved quantity and the quantity in the gaseous phase for each gas. This equilibrium at 25° C. is known for each gas from the partition ratios given in Table 4. The ppm of each gas in the gaseous phase is measured with a gas chromatograph, and from this number the ppm of each gas in the oil originally was calculated.

Figure 5:
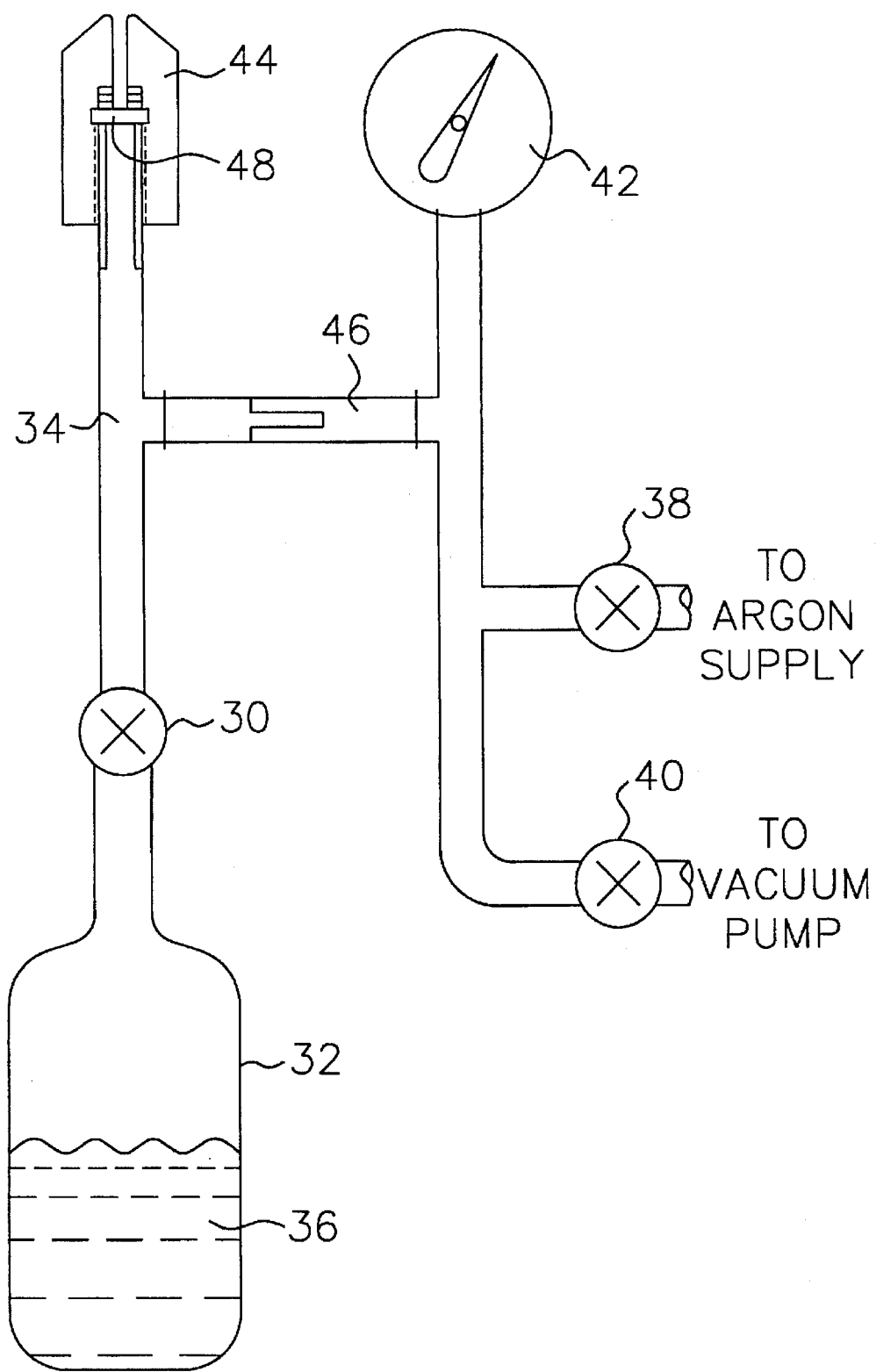
FIG. 5 is a schematic illustration of a system for extracting sample gases dissolved in transformer oil.

A schematic diagram of the system actually used in this method is shown in FIG. 5. The actual procedure with this apparatus is as follows.

(1) Attach the top valve 30 of the 150 cc stainless steel tank 32 to ¼ Swagelok tubing 34 with brass adapter. The tank is filled with transformer oil 36.

(2) With top valve 30 and valve 38 closed, pump out the system through valve 40 until the vacuum gauge 42 reads a good vacuum (~29 inches). Check that there are no leaks. Septum cap 44 must be finger-tight.

(3) Close valve 40 and open valve 38 to argon supply. Argon line should be bled before attaching it to valve 38.

(4) With about 5 psig of argon pressure, open valve 30 and slowly open partly a valve (not shown) at the bottom of the SS tank to drain out about 75 cc of oil. For accurate results, quantity of oil remaining in the tank must be known accurately.

(5) Close all valves, valve 38 last. Pressure should be 5 psig. Disconnect quick connect 46.

(6) Shake the oil in the tank for 5 to 10 minutes for gaseous equilibrium. Reconnect quick connect 46.

(7) Pump out argon from line up to valve 30. Disconnect quick connect.

(8) Open valve 30.

(9) Sample with hypodermic needle through septum 48.

(10) Inject sample into a gas chromatograph (not shown) for measurement.

The results for the ppm in the same oil sample as measured by the mercury Toepler pump method of extraction and the direct analysis method of this Example were compared. These results agreed quite closely. This agreement shows the validity of the present method, which is simpler, faster and safer because no mercury is involved.

Another advantage of the present method over the mercury extraction method is the shorter time required. Total time to go through steps 1 through 10 of the procedure described above can be about 15 minutes. The search for a method that can replace the mercury extraction method is of wide interest in the electric power industry. In addition to the current method, which takes as much as an hour per sample, there is the danger of working with large amounts of mercury in glassware that is under high vacuum. A breakage may release up to 50 lbs. of mercury. Also, as is reported in the literature, due to the dead volume of the extraction system, oils containing very low levels of gas cannot produce enough gas to perform accurate chromatographic analyses. In the handling of the sample the more volatile gases can be lost, particularly hydrogen. Also the possibility exists of sample contamination by the $N_2$ and $O_2$ from air absorption during the extraction process.

In addition to the current method in use, another method consists of an oil stripper column inserted in the oven chamber of the gas chromatograph. Argon carrier gas is employed for the stripping process. The literature has presented a comparison between the mercury extraction and oil stripper methods. The results of measuring nine gases dissolved in transformer oil by the vacuum extraction (mercury) method were compared with the method utilizing a stripper column. In the oil stripper method the gases are sparged out of the oil in the stripper column using the argon carrier gas, before being passed into the GC (gas chromatograph). The stripper column is contained within the oven compartment of the gas chromatograph at a temperature of 75° C. The quantification was performed based on the relative extraction efficiencies for each gas as determined from internally prepared gas in oil standards. The gas response factors were adjusted based on the gas in oil extraction efficiencies. Since the gas solubilities vary with temperature, the extraction efficiencies were different at 75° C. from that at room temperature. This contributes to inaccuracy in the direct injection method and in its calibration runs. The comparative results show a large discrepancy (over 20%) between the direct injection method and vacuum extraction method for many points. For example, hydrogen vacuum extraction yielded 200 ppm, while direct injection yielded 280 ppm. Ethylene vacuum extraction yielded 70 ppm and direct injection yielded 25 ppm, a 64% discrepancy. Acetylene vacuum extraction yielded 31 ppm and direct injection yielded 21 ppm, a 32% discrepancy.

EXAMPLE 3

An experimental test of fault gas concentrations was conducted on a large transformer (11,600 gallons) at an electrical utility site. Direct measurements of the nine gases contained in the headspace above the oil level were made. The results were as follows:

| Gas Species in Transformer Oil | Species Concentration in Gas Blanket (Headspace) over Oil in Transformer (ppm) | Concentration of Gas Species Dissolved in Transformer Oil (ppm) |
| --- | --- | --- |
| Hydrogen, $H_2$ | 346 | 17 |
| Methane, $CH_4$ | 423 | 135 |
| Carbon Monoxide, CO | 314 | 33 |
| Carbon Dioxide, $CO_2$ | 1962 | 1502 |
| Ethylene, $C_2H_4$ | 410 | 469 |
| Ethane, $C_2H_6$ | 32 | 54 |
| Acetylene, $C_2H_2$ | ~0 | ~0 |

Corrections were made for the gas-oil partitions, helium pressure, and oil temperature (49.5° C.).

A Poropak N column was used for $CH_4$, $CO_2$, $C_2H_4$, $C_2H_6$ and $C_2H_2$ (FIG. 2A), and a Molsieve 5A column was used for $H_2$, $CH_4$ and CO (FIG. 2B). Scott standard gas was employed for calibrations. The accuracy limits of the results include ±10% from Scott standard gas for each gas species and chromatographic variability.

The gas analysis indicated that the transformer probably sustained overheating of the oil. Overheated oil exhibits higher concentrations of methane and ethylene, 135 and 469 ppm, respectively. The recommended acceptable limits are approximately 100 ppm for $CH_4$ and 150 ppm for $C_2H_4$. There was no evidence of arcing, as indicated by the low concentration of hydrogen and no measurable concentration of acetylene.

Analysis of the results compared favorably with the results of conventional analysis of an oil sample taken from the same transformer. As can be seen, the concentration in the headspace for important combustibles is far greater (including $H_2$, $CH_4$ and CO) than the concentration in the oil. The present method thus allows small concentrations of these combustibles to be determined whereas they may be overlooked by conventional analysis.

Although the present invention has been described with respect to measuring fault gas concentration levels in a gas chromatograph, the invention also can be carried out with other instruments capable of measuring the amount of each fault gas contained in a gas sample taken from the headspace of a transformer. A mass spectrometer is an example of another instrument that could be used in the process of this invention. Electrical resistance measuring devices for measuring individual gas concentrations also can be used.

In addition to the on-line system described above, in which gas analysis is conducted in a completely automated system for utilities with transformer banks, the invention also can be carried out in a portable system, in which a portable gas chromatograph is taken to the transformer site for measuring fault gases in individual transformers, for example. Off-the-shelf gas chromatographs using the present method also can be used to replace current laboratory gas analysis systems. In one embodiment, a laboratory method can be carried out using an oil sample from the transformer under test, in which the test equipment and procedure of FIG. 5 are used to generate a headspace gas sample which is then input to the gas chromatograph for measuring fault gas concentrations.

I claim:

1. A method for monitoring dissolved gases in the electrical insulating oil supply of an electrical transformer in which a blanket of ambient gas containing a plurality of fault gases is present in an equilibrium state in the headspace above the insulating oil supply contained in the transformer, the method comprising:

withdrawing from the headspace a sample of the ambient gas present in the headspace and transferring the withdrawn gas sample to an instrument for measuring the amounts of particular fault gases present in the gas sample;

operating said instrument for measuring the gas concentration levels of the fault gases contained in the gas sample;

applying fault gas measurement values determined by said instrument as an input to a programmed computing device informed of a gas temperature and pressure dependent gas partition function between the headspace gas and the oil-dissolved fault gases based on gas solubility and gas/liquid equilibrium constraints according to Henry's Law;

determining the temperature and pressure of the ambient gas within the headspace, informing the programmed computer of said gas temperature and pressure information so that gas temperature and pressure corrections can be made according to the ideal gas law for the ambient gas within said headspace, and using said gas temperature and pressure information as an input to the gas partition function;

calculating the related gas concentration levels of said fault gases which are present in the transformer oil supply by operating the computing device in relation to said partition function to convert fault gas concentration levels in the headspace to related measurements of the concentration level of particular fault gases in the transformer oil supply; and thereafter producing a reading of the calculated fault gas concentration in the transformer oil supply to provide an indication of a specific transformer fault.

2. The method according to claim 1 in which the instrument is a gas chromatograph.

3. The method according to claim 2 in which the fault gas concentrations are each measured by the gas chromatograph instrument and converted by said programmed computing device into separate related measurements of the concentration levels of the same fault gases contained in the transformer oil supply.

4. The method according to claim 3 in which the computer is informed of a safe concentration level of each fault gas concentration measurement and provides an alarm signal if a safe level is exceeded.

5. The method according to claim 1 including transmitting gas samples from the headspace of a plurality of transformers in sequence to a common gas chromatograph instrument for producing said calculations.

6. The method according to claim 5 including calculating the fault gas concentration levels in the oil supplies of the plurality of transformers via the common gas chromatograph instrument, and transmitting the calculated fault gas concentration levels in said oil supplies to a common display.

7. The method according to claim 1 in which the headspace gas sample is generated from transferring an oil sample under test to a closed open-volume container used to produce the headspace gas as a gas blanket above the oil sample.

8. A method for detecting the gas concentration levels of fault gases evolved in a supply of electrical insulating oil contained in an electrical transformer in which the transformer housing contains a fault gas-containing ambient gas blanket in an equilibrium state in a headspace above the insulating oil supply, the method comprising:

transferring a sample of the ambient gas contained in the headspace to a gas chromatograph instrument;

operating the instrument to measure the concentration levels of the fault gases contained in the gas sample;

informing a programmed computer device of the measured fault gas concentration levels;

determining the temperature and pressure of the ambient gas contained in the headspace of the transformer;

informing the programmed computer device of a fault gas temperature and pressure-related partition function between the headspace gas and the oil-dissolved fault gases based on gas solubility and gas/liquid equilibrium constraints according to Henry's Law;

providing the fault gas temperature and pressure information as inputs to the partition function means of the programmed computer device so that gas temperature and pressure corrections can be made according to the ideal gas law for the ambient gas within the headspace;

operating the programmed computer device for converting a measured fault gas concentration level in the gas sample taken from the transformer headspace to a related gas concentration level of the same fault gas contained within the transformer oil supply and calculating the concentration levels of the fault gases contained in the transformer oil supply; and providing said calculated fault gas concentration levels as an output representing a specific fault condition of the transformer.

9. The method according to claim 8 including transmitting gas samples from the headspaces of a plurality of transformers in sequence to a common gas chromatograph instrument.

10. The method according to claim 8 in which the gas in the transformer headspace contains a plurality of separate fault gases, and in which the partition function of the computer device is programmed to calculate the concentration levels of each of said fault gases contained in the transformer oil supply from the gas sample transmitted from the transformer headspace.

11. The method according claim 10 including programming the computer device with separate safe ranges of gas concentration levels for each fault gas, comparing the measured concentration level of each fault gas with the safe range data, and providing an alarm if a measured fault gas concentration level exceeds the safe range.

12. The method according to claim 8 in which the headspace gas sample is generated from transferring an oil sample under test to a container used to produce the headspace gas as a gas blanket above the oil sample.

13. A system for monitoring dissolved gases in the electrical insulating oil supply of an electrical transformer in which a blanket of ambient gas containing a plurality of fault gases is present in an equilibrium state in the headspace above the insulating oil supply contained in the transformer, the system comprising:

an instrument for measuring the concentration levels of particular fault gases present in the gas sample;

a programmed computing device informed of a gas temperature and pressure dependent gas partition function between the headspace gas and the oil-dissolved fault gases based on gas solubility and gas/liquid equilibrium constraints according to Henry's Law;

means for determining the temperature and pressure of the ambient gas within the headspace and providing said gas temperature and pressure information as inputs to the partition function so that gas temperature and pressure corrections can be made by the programmed computing device according to the ideal gas law for said ambient gas;

said computing device programmed for calculating the related gas concentration levels of said fault gases which are present in the transformer oil supply based on said partition function; and means for producing a computerized interpretation of the fault gas concentrations in the transformer oil supply to provide an indication of a specific transformer fault.

14. The system according to claim 13 in which the instrument is a gas chromatograph.

15. The system according to claim 13 in which the headspace contains a plurality of fault gases, and the fault gas concentrations are each measured by the instrument and converted into separate related measurements of the concentration levels of the same fault gases contained in the transformer oil supply, and means for providing readings of the fault gas concentration levels in the transformer oil supply.

16. The system according to claim 15 in which the computer is informed of a safe concentration level of each fault gas concentration measurement and provides an alarm signal if a safe level is exceeded.

17. The system according to claim 13 and further comprising a plurality of electrical transformers configured to conduct remote gas analysis from each of a plurality of separate sites, and conduit and timer valve means for transmitting ambient gas samples from the headspace of a plurality of transformers in sequence to a common instrument for producing said calculations.

18. The system according to claim 15 including means for calculating the fault gas concentration level in the oil supplies of the plurality of transformers via the common instrument, and transmitting the calculated fault gas concentration levels in said oil supplies to a common display.

19. The system according to claim 13 in which the headspace gas sample is generated from transferring an oil sample under test to a container used to produce the headspace gas as a gas blanket above the oil sample.

20. A system for detecting the gas concentration levels of fault gases evolved in a supply of electrical insulating oil contained in an electrical transformer in which the transformer housing contains an ambient fault gas-containing gas blanket in an equilibrium state in a headspace above the insulating oil supply, the system comprising:

a gas chromatograph instrument for measuring the concentration levels of fault gases contained in the gas sample;

means for informing a programmed computer device of the measured fault gas concentration levels;

means for informing the computer device of a fault gas temperature and pressure-related partition function between the headspace gas and the gas-dissolved fault gases based on gas solubility and gas/liquid equilibrium constraints according to Henry's Law to provide means for converting a measured fault gas concentration level in the ambient gas sample taken from the transformer headspace to a related gas concentration level of the same fault gas contained within the transformer oil supply;

means for determining the temperature and pressure of the ambient gas within the headspace and providing such fault gas temperature and pressure information as inputs to the partition function means of the computer device so that gas temperature and pressure corrections can be made according to the ideal gas law for said ambient gas; and means for operating the computer device for calculating the concentration levels of the fault gases contained in the transformer oil supply, said calculated fault gas concentration levels comprising an output having a computerized interpretation representing a specific fault condition of the transformer.

21. The system according to claim 20 including transmitting gas samples from the headspaces of a plurality of transformers in sequence to a common gas chromatograph instrument.

22. The system according to claim 20 in which the gas in the transformer headspace contains a plurality of separate fault gases, and in which the partition function of the computer device is programmed to calculate the concentration levels of each of said fault gases contained in the transformer oil supply from the gas sample transmitted from the transformer headspace.

23. The system according claim 20 including means for programming the computer device with separate safe ranges of gas concentration levels for each fault gas, and means for comparing the measured concentration level of each fault gas with the safe range data, and means providing an alarm if a measured fault gas concentration level exceeds the safe range.

24. The system according to claim 20 in which the headspace gas sample is generated from transferring an oil sample under test to a container used to produce the headspace gas as a gas blanket above the oil sample.

25. A method for monitoring dissolved gases in the electrical insulating oil supply of an electrical transformer in which a blanket of gas containing a fault gas is present in the headspace above the insulating oil supply contained in the transformer, the method comprising:

producing a sample of the gas contained in the headspace and transferring the gas sample to an instrument for measuring the amount of a particular fault gas present in the gas sample;

operating said instrument for measuring the gas concentration level of the fault gas contained in the gas sample;

applying a fault gas measurement value determined by said instrument as an input to a programmed computing device informed of a gas temperature and pressure dependent gas partition function between the headspace gas and the oil-dissolved gas based on gas solubility and gas/liquid equilibrium constraints according to Henry's Law;

measuring the temperature and pressure of the gas within the headspace of the transformer, informing the computer of the measured gas temperature and pressure information, and using the temperature and pressure information as an input to the gas partition function to calculate the fault gas concentration level in the transformer oil supply;

calculating the related gas concentration level of said fault gas which is present in the transformer oil supply by operating the computing device in relation to said partition function to convert said fault gas concentration level in the headspace to a related measurement of the concentration level of said fault gas in the transformer oil supply;

thereafter producing a reading of the fault gas concentration in the transformer oil supply to provide an indication of a specific transformer fault;

including transmitting gas samples from the headspace of a plurality of transformers in sequence to a common gas chromatograph instrument for producing said calculations; and calculating the fault gas concentration level in the oil supplies of the plurality of transformers via the common instrument, and transmitting the calculated fault gas concentration levels in said oil supplies to a common display.

26. A system for monitoring dissolved gases in the electrical insulating oil supply of an electrical transformer in which a blanket of gas containing a fault gas is present in the headspace above the insulating oil supply contained in the transformer, the system comprising:

an instrument for measuring the amount of a particular fault gas present in a gas sample taken from the headspace;

a programmed computing device informed of a gas temperature and pressure dependent gas partition function between the headspace gas and the oil-dissolved gas based on gas solubility and gas/liquid equilibrium constraints according to Henry's Law, said computing device programmed for calculating the related gas concentration level of said fault gas which is present in the transformer oil supply based on said partition function to convert an output of said instrument to a measurement of the concentration level of said fault gas in the transformer oil supply; and means for producing, interpreting and electronically analyzing a reading of the fault gas concentration in the transformer oil supply to provide an indication of a specific transformer fault, including means for calculating the fault gas concentration level in the oil supplies of the plurality of transformers via the common instrument, and transmitting the calculated fault gas concentration levels in said oil supplies to a common display.

27. The system according to claim 26 in which the computer device is informed of a safe concentration level of each fault gas concentration measurement and provides an alarm signal if a safe level is exceeded.

* * * * *